US009446201B2

(12) United States Patent
Holmqvist (10) Patent No.: US 9,446,201 B2
(45) Date of Patent: Sep. 20, 2016

(54) MEDICAMENT DELIVERY DEVICE (75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 621 days.

(21) Appl. No.: 13/642,524

(22) PCT Filed: Apr. 14, 2011

(86) PCT No.: PCT/SE2011/050458
§ 371 (c)(1),
(2), (4) Date: Oct. 20, 2012

(87) PCT Pub. No.: WO2011/136718
PCT Pub. Date: Nov. 3, 2011

(65) Prior Publication Data
US 2013/0041322 A1 Feb. 14, 2013

Related U.S. Application Data (60) Provisional application No. 61/327,748, filed on Apr. 26, 2010.

(30) Foreign Application Priority Data

Apr. 26, 2010 (SE) ...................................... 1050409

(51) Int. Cl.
A61M 5/00 (2006.01)
A61M 5/315 (2006.01)
A61M 5/20 (2006.01)

(52) U.S. Cl.
CPC ............ *A61M 5/31525* (2013.01); *A61M 5/20* (2013.01); *A61M 5/3155* (2013.01);
(Continued)

(58) Field of Classification Search
CPC ............. A61M 5/31; A61M 5/31533; A61M 5/31548; A61M 5/3155; A61M 5/31553; A61M 2005/3125; A61M 5/20; A61M 5/24; A61M 5/315; A61M 5/31501; A61M A61M 5/3159; A61M 5/31593; A61M 5/31525;
A61M 5/31558; A61M 5/31283; A61M 2005/202; A61M 2005/2006; A61M 2005/3126
USPC ......................................... 604/207, 211, 246
See application file for complete search history.

(56) References Cited

U.S. PATENT DOCUMENTS

2004/0054326 A1   3/2004 Hommann et al.
2004/0064104 A1*  4/2004 Miller ............... A61M 5/31525
                                                          604/207
(Continued)

FOREIGN PATENT DOCUMENTS

WO    9810813 A1    3/1998
WO    9856436 A1   12/1998

OTHER PUBLICATIONS

Swedish Patent Office, Int'l Search Report in PCT/SE2011/050458, Jul. 22, 2011.
(Continued)

*Primary Examiner* — Edelmira Bosques
*Assistant Examiner* — Leah Swanson
(74) *Attorney, Agent, or Firm* — Piedmont Intellectual Property (57) ABSTRACT A medicament delivery device has proximal and distal housing parts connected along a longitudinal axis, the proximal part for accommodating a medicament container. A drive member inside the distal part has a first circumferential set of interacting devices. A longitudinal plunger rod is rotationally locked through a central passage of the distal part, acts on a stopper inside the container, and is connected to the plunger rod. A turnable dose setting member coaxially arranged around the drive member is rotatably connected to the distal part. A torsion spring is connected to the dose setting member and to a hub of the drive member. The hub, spring, dose setting member, and drive member are coaxial transversally. The drive nut has second interacting devices on its outer surface. When the drive member is rotated by the spring, the drive nut rotates, whereby the plunger rod moves proximally for expelling a dose of medicament.

12 Claims, 6 Drawing Sheets

(56) References Cited

U.S. PATENT DOCUMENTS

| | | | |
|---|---|---|---|
| 2006/0276754 A1* | 12/2006 | Kronestedt et al. | 604/186 |
| 2009/0318865 A1* | 12/2009 | Moller et al. | 604/135 |
| 2013/0096495 A1* | 4/2013 | Holmqvist | A61M 5/2033 604/89 |

OTHER PUBLICATIONS

Swedish Patent Office, Written Opinion in PCT/SE2011/050458, Jul. 22, 2011.

* cited by examiner

MEDICAMENT DELIVERY DEVICE

TECHNICAL AREA

The present invention relates to a medicament delivery device capable of delivering doses of medicament preset by a user, and in particular a device which is easy and intuitive to use regarding both setting of dose and delivery of dose.

TECHNICAL BACKGROUND

There are today numerous medicament delivery devices on the market where the main intention is to use them for self-administration of medicament. The patient or user should thus be able to use the device, whereby the device should be easy and intuitive to use for a wide range of patients from children to elderly as well as persons with reduced dexterity of the hands.

In many instances it is an advantage that different doses may be set individually by the user. This could for example be that a user should take different doses during a medication period or that the same device could be used for different persons requiring different doses, such as children and adults requiring different quantities of medicament.

It could also be an advantage that the force member, such as a spring, acting on a medicament container in order to expel a dose, is tensioned when a dose is set. In this way the device does not have to be stored in a highly tensioned state as often is the case with devices using spiral compression springs. Thus, the risk of damage to the devices due to creeping effects in the materials of the device is greatly reduced.

With this type of function some devices have been utilizing torsion springs as strip spiral springs, or clock springs, that are wound in a spiral having a central passage in which a hub is placed. Document WO 2008/155144 discloses a medicament delivery device arranged with a strip clock spring. The spring is arranged transversal in relation to the longitudinal direction of the device and is tensioned by turning a knob at the distal end of the device. The use of a torsion spring in this fashion means that the distal end of the device becomes rather bulky with a much larger diameter than the proximal part of the device. Further the placement of a dose setting knob is limited to the distal end of the device.

For some applications this design is not optimal and it would be advantageous to have another design and position of the dose setting knob or wheel, which may be more intuitive. Documents WO 9856436 and WO9810813 disclose a medicament delivery device provided with a dose setting wheel having an axis of rotation generally perpendicular to the longitudinal direction of the device. The intention with this design is to provide a dose setting mechanism allowing larger digits or numbers to be displayed as well as a larger dose setting wheel which in total facilitates the dose setting for persons with impaired sight and/or dexterity in their hands. However, when a dose is to be delivered, the mechanism is completely manual and the user has to press a dose delivery button on the distal end of the device. The manual actuation of the dose delivery is however not optimal for persons with weak hands, and in particular if the medicament is of higher viscosity than water, which requires higher forces to push the medicament through a medicament delivery member such as an injection needle. There is thus room for improvement of the state of the art medicament delivery devices.

BRIEF DESCRIPTION OF THE INVENTION

The aim of the present invention is to remedy the drawbacks of the state of the art devices and to provide a medicament delivery device that is easy to handle both regarding setting of dose, handling of the device during dose delivery and further that also is capable of handling medicaments with higher viscosity.

This aim is obtained by a medicament delivery device defined by the features of the independent patent claim.

Preferable features of the invention form the subject of the dependent patent claims.

According to a main aspect of the invention, it is characterised by a medicament delivery device having a longitudinal axis and a transversal axis, wherein the device comprises a proximal and a distal housing part connected to each other and extending along the longitudinal axis, wherein the proximal housing part is arranged to accommodate a medicament container; a drive member rotatable arranged inside the distal housing part and comprising a first circumferentially extending set of interacting means; a threaded plunger rod extending along the longitudinal axis, being rotationally locked through a central passage of the distal housing part and arranged to act on a stopper inside said medicament container; a threaded drive nut threadedly connected to said plunger rod; a turnable dose setting member coaxially arranged around the drive member and rotatably connected to the distal housing part; a torsion spring having a first end connected to the turnable dose setting member and a second end connected to a central hub of the drive member; wherein the hub, the torsion spring, the turnable dose setting member and the drive member are coaxially arranged about the transversal axis which is generally perpendicular to the longitudinal axis, and in that said threaded drive nut 36 is arranged with second interacting means on its outer surface cooperating with the first circumferentially extending set of interacting means such that when said drive member is forced to rotate by said torsion spring, the drive nut is also rotated whereby the plunger rod is moved in the proximal direction for expelling a dose of medicament.

According to another aspect of the invention, it further comprises an activation mechanism having an actuatable member with a lock member interactively connected to the second interacting means of the drive nut for locking said drive nut from rotation until an activation of the actuatable member is performed by a user.

According to yet another aspect of the invention, the turnable dose setting member comprises a circumferentially extending ratchet arranged to co-act with a corresponding circumferentially extending ratchet arranged on the distal housing part, and wherein said ratchets are form shaped such that said dose setting member is only rotated in one direction.

According to a further aspect of the invention, said dose setting member is resiliently movable in the longitudinal direction of the hub by a first resilient member which is arranged between a circumferential ledge of the distal housing part and a circumferential ledge of the dose setting member for forcing said ratchets in connection with each other, such that when said dose setting member is pulled against the force of said first resilient member, the ratchets move out of contact with each other and the dose setting member may be turned back to reset a dose.

According to yet a further aspect of the invention, indicia is arranged on the outer circumferential surface of the drive member and which indicia is visible through a window on the circumferential surface of the dose setting member.

According to another aspect of the invention, the second end of the torsion spring is connected to the central hub of the drive member through a lock sleeve.

According to yet another aspect of the invention, the torsion spring is a clock spring.

There are a number of advantages with the present invention. With the positioning of the dose setting member, the torsion spring, the drive member and its hub generally perpendicular to the longitudinal direction of the plunger rod, a different design is obtained whereby a user in a very easy way can set the dose and at the same time tension the spring and when the device is activated, an automated medicament delivery is obtained when the drive member rotates the drive nut due to the cogs cooperating with each other. Thus a torsion spring, which is very useful for different applications, and in particular for tensioning it just prior to drug delivery, is used in a novel way.

Also, with this design, the activation mechanism may be placed on several positions along the device, providing a freedom of design depending on application. Preferably the drive member is arranged with indicia visible through a window such that when the dose setting member is turned in relation to the drive member, it is possible to view the set dose. Because of the use of ratchets, it is possible to turn the dose setting member in one direction and when the dose setting member is released, it is held in that position. However, the device is arranged with resetting means which is an advantage if a too large dose has been set.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

In the present application, the wording generally perpendicular is defined as the intersection between a transversal and longitudinal axis forming an acute angle of at least 45 degrees.

According to the invention, a medicament delivery device have a longitudinal axis 17 and a transversal axis 15, wherein the device comprises a proximal 10 and a distal 24 housing part connected to each other and extending along the longitudinal axis, wherein the proximal housing part is arranged to accommodate a medicament container 14; a drive member 46 rotatable arranged inside the distal housing part and comprising a first circumferentially extending set of interacting means 44; a threaded plunger rod 26 extending along the longitudinal axis, being rotationally locked through a central passage 32 of the distal housing part and arranged to act on a stopper 28 inside said medicament container; a threaded drive nut 36 threadedly connected to said plunger rod; a turnable dose setting member 70 coaxially arranged around the drive member and rotatably connected to the distal housing part; a torsion spring 68 having a first end connected to the turnable dose setting member and a second end connected to a central hub 58 of the drive member; wherein the hub, the torsion spring, the turnable dose setting member and the drive member are coaxially arranged about the transversal axis which is generally perpendicular to the longitudinal axis, and in that said threaded drive nut 36 is arranged with second interacting means 42 on its outer surface cooperating with the first circumferentially extending set of interacting means such that when said drive member is forced to rotate by said torsion spring, the drive nut is also rotated whereby the plunger rod is moved in the proximal direction for expelling a dose of medicament.

An exemplary embodiment of the present invention is shown in the FIGS. 1-6. The medicament delivery device shown in the exemplary embodiment comprises the proximal housing part 10 provided with a proximal threaded neck 12 onto which a medicament delivery member (not shown) may be attached, such as an injection needle, a mouth or nose piece, a nozzle and the like. It is in this context to be understood that other types of attachment mechanisms may be employed, having the same function. The proximal housing part 10 is arranged to accommodate the medicament container 14 whereby the proximal housing part is arranged with openings 16 so that the medicament container 14 may be viewed and preferably the medicament inside the container if the container 14 is transparent. A protective cap 18 is arranged to be attached onto the neck 12. The proximal housing part 10 is further arranged with attachment means 20 on its inner distal surface area, FIG. 4, which attachment means 20 are arranged to cooperate with a corresponding attachment means 22 on the distal housing part 24.

Figure 3:
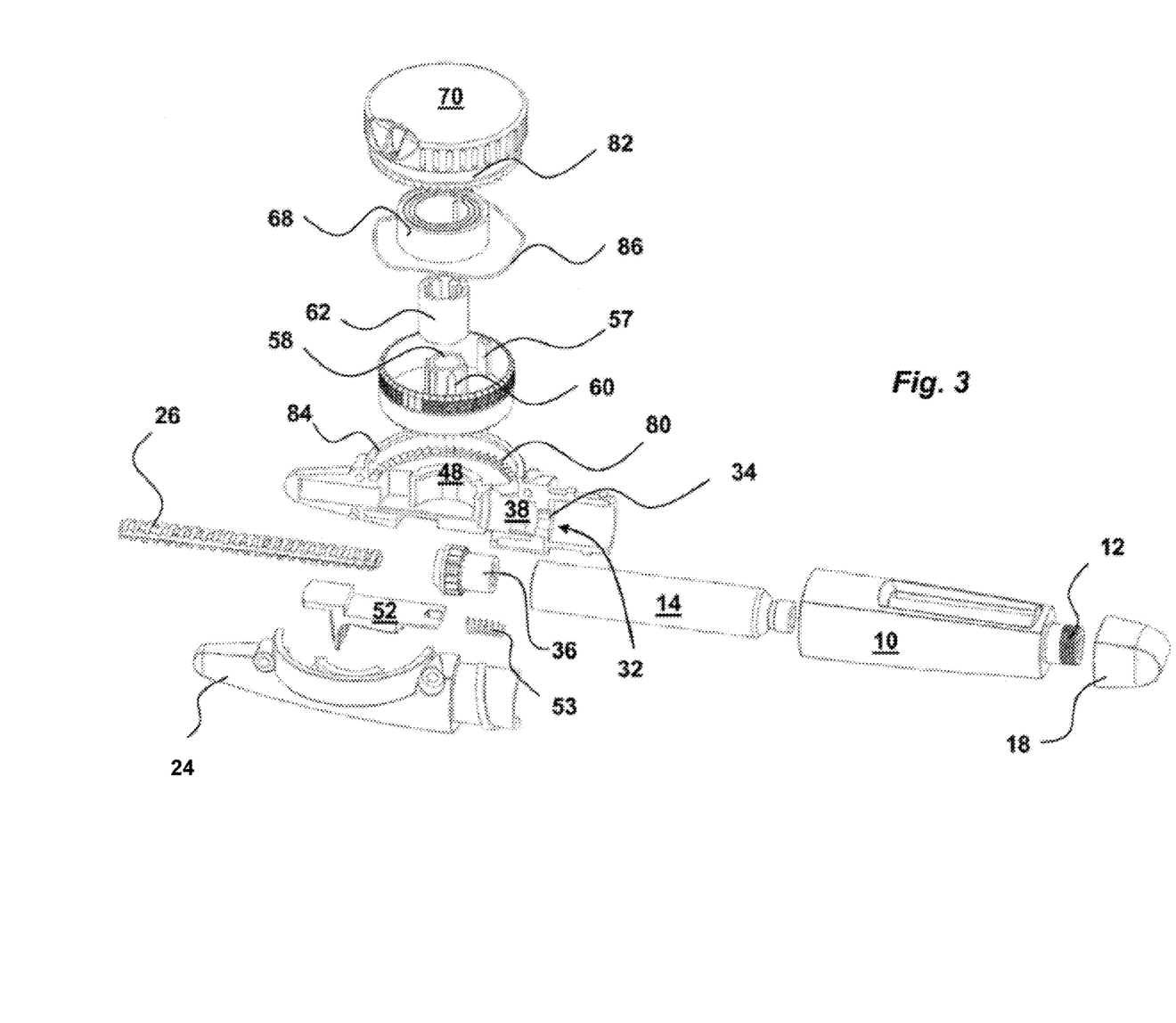
FIG. 3 is an exploded view of the device of FIG. 1 turned 180° in relation to FIG. 2.
Figure 4:
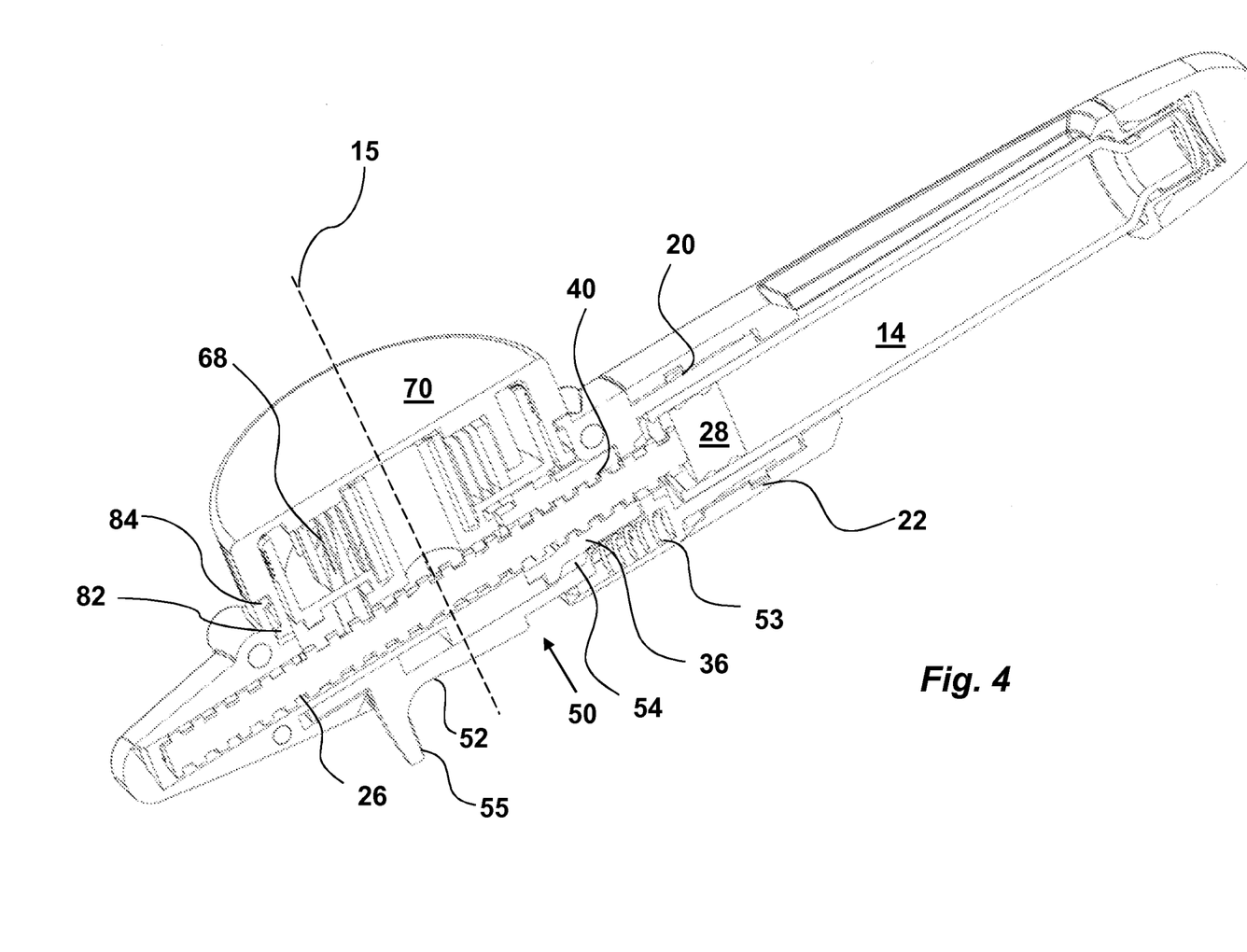
FIG. 4 is a cross-sectional view of the device of FIG. 1.

Inside the distal housing part 24 the elongated threaded plunger rod 26 is arranged with its proximal end in contact with the movable stopper 28, FIG. 4, inside said medicament container 14. The plunger rod 26 is arranged with longitudinally extending grooves 30, FIG. 5, and protrudes through the central passage 32 in the distal housing part, FIG. 3, which passage 32 is arranged with radially inwardly extending protrusions 34, which fit into the grooves 30 of the plunger rod 26, in order to obtain a rotational lock of the plunger rod 26 but allowing a longitudinal movement.

Figure 2:
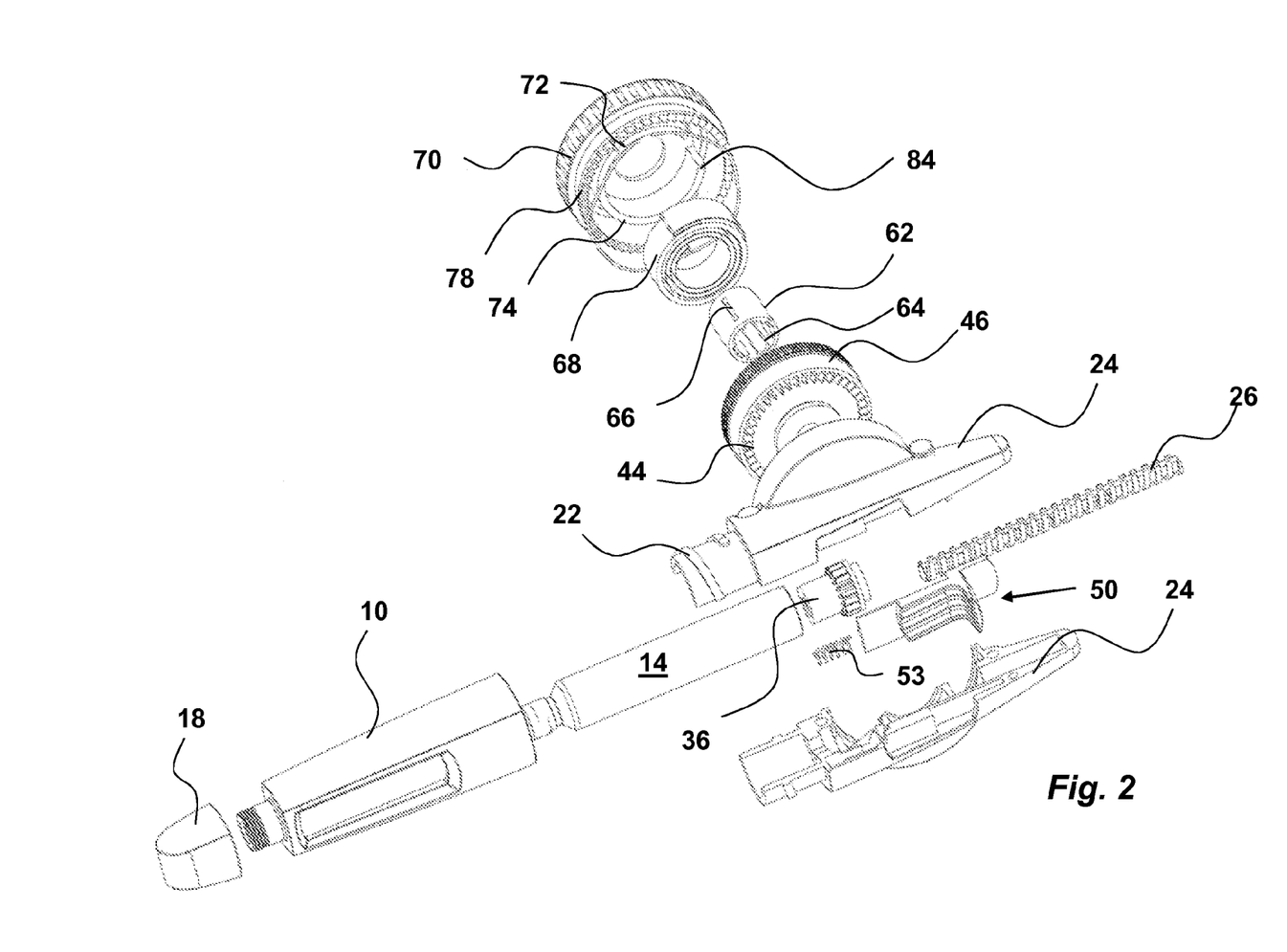
FIG. 2 is an exploded view of the device of FIG. 1.

Further the generally sleeve-shaped drive nut 36 is rotationally arranged in a seat 38, FIG. 3, of the distal housing part 24, which drive nut 36 is arranged with threads 40, FIG. 4, corresponding to the threads of the plunger rod 26. In the exemplary embodiment, the second interacting means as e.g. a number of cogs 42 are arranged on the outer circumferential surface of the drive nut 36, FIG. 5. These second interacting means 42 cooperate with the first circumferentially extending set of interacting means 44 as e.g. a circumferentially extending set of cogs 44 on the circumference of a lower surface of the drive member 46 embodied as a drive wheel, which drive member 46 is positioned in a seat 48 of the distal housing part 24, FIG. 2.

In the exemplary embodiment, as shown in FIG. 4, an activation mechanism 50 is further arranged in the device. It comprises an actuatable member 52 slidably arranged in the distal housing part and arranged to be pushed in the distal direction by a second resilient member 53. The actuatable member 52 further comprises a lock member 54 in the form of a protrusion arranged to engage the cogs 42 of the drive nut 36. The activation mechanism 50 further comprises a gripping part 55 radially protruding out of the distal housing part. In this context it is to be understood that the activation mechanism may have other configurations such that it is pivotable instead of slidable, that the protruding actuation member may have other designs or may be placed on other locations on the device.

Figure 5:
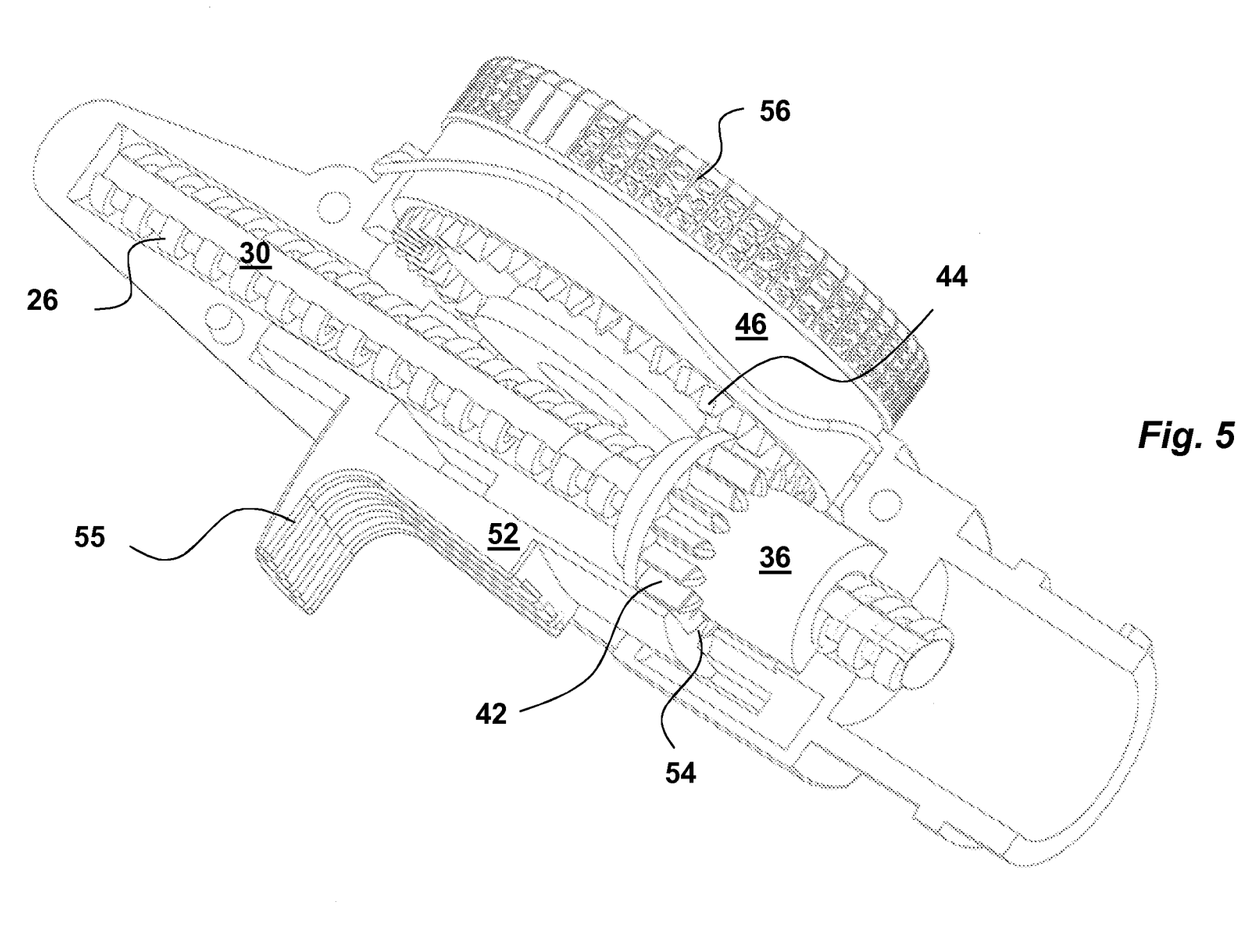
FIG. 5 is a detailed view in perspective of the device of FIG. 1 with some components removed for clarity.

In the exemplary embodiment, as shown in FIGS. 3 and 5, the outer circumferential surface of the drive member 46 is arranged with indicia 56, such as numbers that correspond to a certain dose quantity. The inner circumferential surface of the drive member is arranged with a stop ledge 57. The centre of the drive member 46 comprises the hub 58 having longitudinally extending ribs 60.

In the exemplary embodiment as shown in FIG. 2, a generally tubular lock sleeve 62 is further arranged to the device having longitudinal grooves 64 on its inner surface, which grooves 64 cooperate with the longitudinal ribs 60 of the hub 58 of the drive member 46. The lock sleeve 62 is further arranged with a slit 66 in which an inner end of a torsion spring 68 is attached. Alternatively, the inner end of the torsion spring 68 may be directly connected to the hub 58. The outer end of the torsion spring 68 is attached to the turnable dose setting member 70, here embodied as a dose setting wheel, where an outer end of the torsion spring is attached to a slit 72 of a circumferential ledge 74 on the inner surface of the dose setting member 70.

Figure 1:
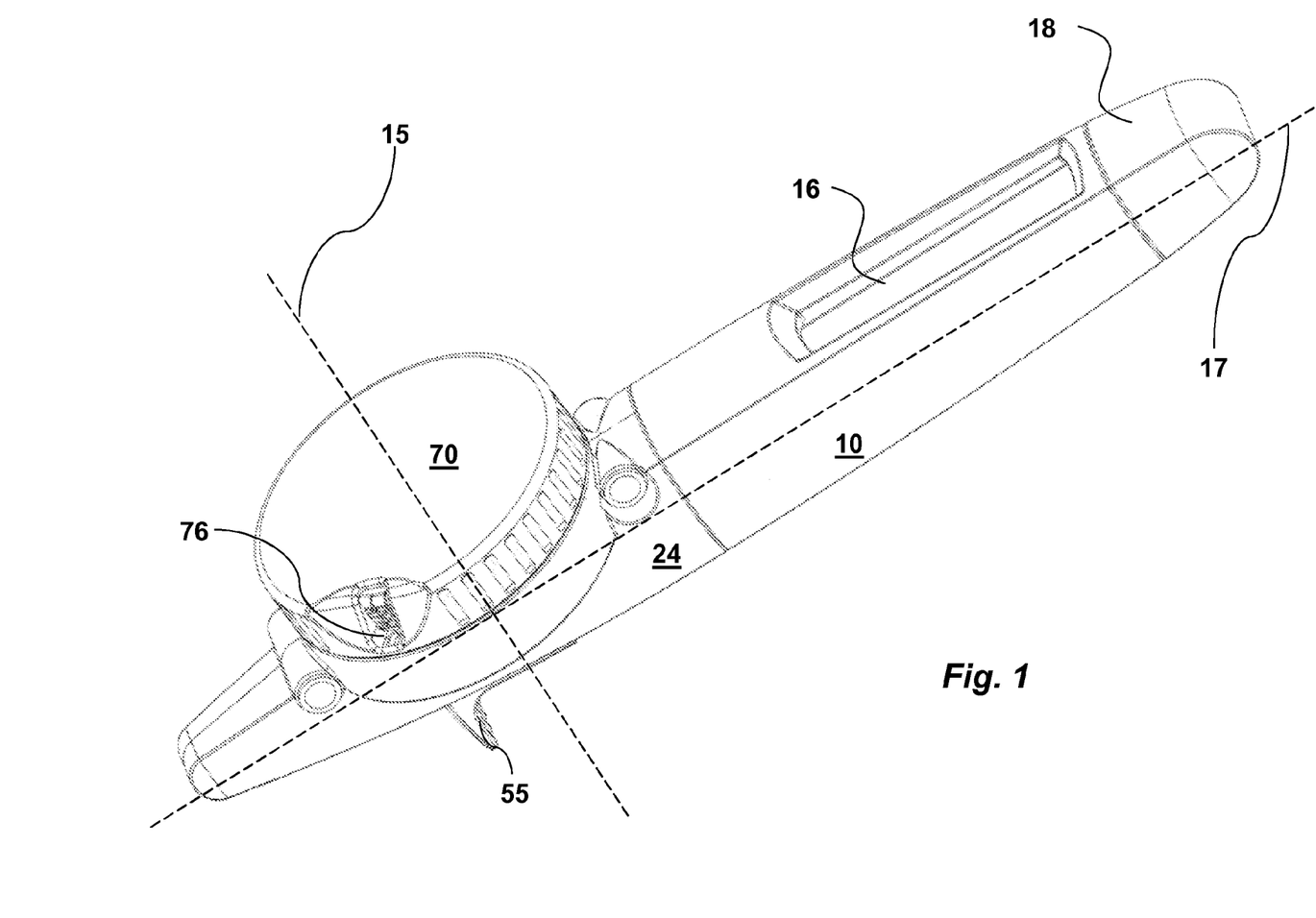
FIG. 1 is a perspective view of a medicament delivery device according to the present invention.
Figure 6:
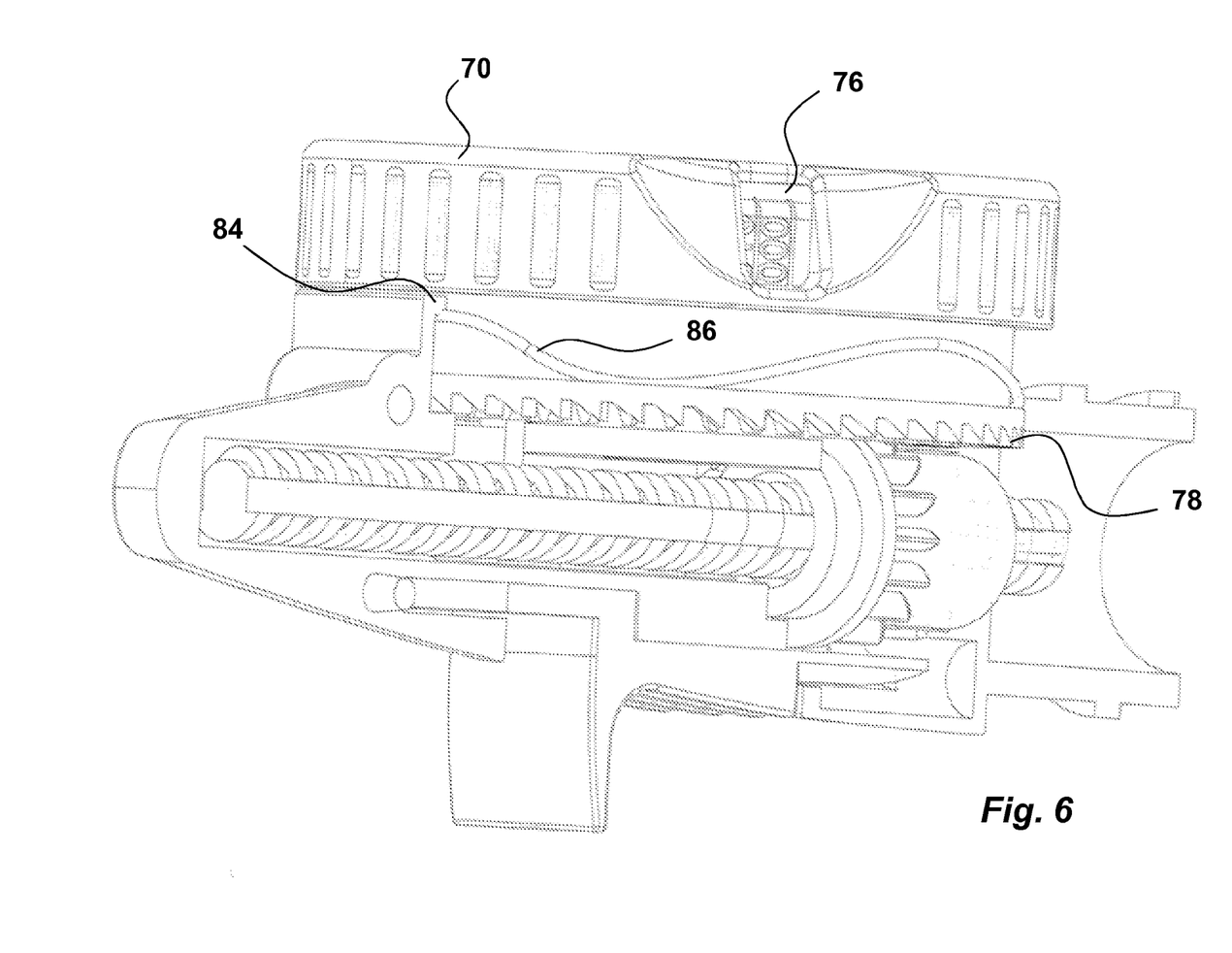
FIG. 6 is yet a detailed view in perspective.

Further the dose setting member 70 is coaxially arranged around the drive member 46 and is arranged with a window 76, FIGS. 1 and 6, for viewing the indicia 56 on the drive member 46, as will be explained. The dose setting member 70 is further arranged with a circumferentially extending one-direction ratchet 78, FIG. 2, which is arranged to cooperate with a one-way circular ratchet 80, FIG. 3, arranged on the surface of the seat 48. In the exemplary embodiment the torsion spring is a clock spring.

In the exemplary embodiment as shown in FIG. 4, the dose setting member 70 is resiliently movable in the longitudinal direction of the hub 58 by a first resilient member 86 which is arranged between a circumferential ledge 84 of the seat 48 of distal housing part and a circumferential ledge 82 of the dose setting member for forcing said ratchets 78, 80 in connection with each other, such that when said dose setting member 70 is pulled in relation to the distal housing part against the force of said first resilient member 86, the ratchets 78, 80 move out of contact with each other and the dose setting member may be turned back to reset a dose.

The device is intended to function as follows. When the device is to be used a medicament container 14 is placed in the proximal housing part 10 and then the two housing parts 10, 24 are attached to each other. Next, the protective cap 18 is removed and a medicament delivery member is attached to the neck 12 of the proximal housing part 10. Then the dose setting member 70 is turned in relation to the distal housing part. The first quantity to be expelled may, depending on the drug, be a priming quantity in order to remove any air trapped inside the container or be a dose to be delivered to a patient.

In any event, the user is beforehand instructed how far the dose setting member 70 should be turned, which is displayed in the window 76, preferably showing indicia 56 regarding an actual set dose volume. Because of the design of the first and second circumferential ratchets 78, 80, the teeth of the ratchets ride over each other against the force of the first resilient member 86 in the dose setting direction. However, if the user releases the grip of the dose setting member 70, it is locked in that position by the design of the teeth of the ratchets 78, 80. Should the user accidentally have turned the dose setting member 70 past a prescribed dose, it is possible to turn the dose setting member 70 back by pulling the dose setting member 70 against the force of the spring 86 whereby the teeth of the ratchets 78, 80 move out of contact with each other, enabling a turning of the dose setting member 70 in the opposite direction.

Further, the distance between two subsequent teeth of said ratchets correspond to a dose increment.

When setting a dose, the turning of the dose setting member 70 causes the torsion spring 68 to be tensioned because the outer end of the torsion spring is attached to the dose setting member 70, and where the inner end of the torsion spring 68 is attached to the slit 66 of the lock sleeve 62. The lock sleeve 62 is locked against rotation because its grooves 64 cooperate with the ribs 60 on the hub 58 of the drive member 46, which in turn is locked against rotation because the engagement between its cogs 44 and the cogs 42 of the drive nut 36, which in turn is locked by the lock member 54 of the activation mechanism 50.

When now a dose of medicament is to be delivered, the user pushes the gripping part 55 in the proximal direction against the force of the spring 53, whereby the lock member 54 moves out of engagement with the cogs 42 of the drive nut 36. The drive nut 36 is now free to rotate and will do so because the drive member 46 is forced to turn by the torsion spring 68 and because of the connection between the cogs 42 of the drive nut 36 and the cogs 44 of the drive member 46. The rotation of the drive nut 36 causes the plunger rod 26 to be advanced in the proximal direction because it is locked against rotation by the protrusions 34 fitting into the grooves 30 of the plunger rod 26. The advancement of the plunger rod 26 causes the stopper 28 to be moved in the proximal direction inside the medicament container 14, whereby a dose of medicament is expelled through the medicament delivery member. The movement of the drive member 46 is stopped when the stop ledge 57 abuts a corresponding stop ledge (not shown) on the circumferential ledge 74 of the dose setting member 70. The medicament delivery member can now be removed and discarded, and the protective cap 18 can be attached to the neck 12 of the proximal housing part 10. When a subsequent dose of medicament is to be delivered, the user again follows the above steps until the medicament container 14 is emptied.

It is to be understood that the embodiment described above and shown in the drawings is to be regarded only as a non-limiting example of the present invention and that it may be amended in many ways within the scope of the patent claims.

The invention claimed is:

1. A medicament delivery device having a longitudinal axis and a transversal axis, comprising:
 a proximal housing part and a distal housing part connected to each other and extending along the longitudinal axis, wherein the proximal housing part is configured to accommodate a medicament container;

a drive member rotatably arranged inside the distal housing part and having a first circumferentially extending set of interacting devices;

a threaded plunger rod extending along the longitudinal axis, rotationally locked through a central passage of the distal housing part, and configured to act on a stopper inside the medicament container;

a threaded drive nut threadedly connected to the plunger rod;

a turnable dose setting member coaxially arranged around the drive member and rotatably connected to the distal housing part;

a torsion spring having a first end connected to the turnable dose setting member and a second end connected to a central hub of the drive member;

wherein the central hub, torsion spring, turnable dose setting member, and drive member are coaxially arranged on the transversal axis, which is generally perpendicular to the longitudinal axis; and the threaded drive nut includes second interacting devices on its outer surface cooperating with the first circumferentially extending set of interacting devices such that when the drive member is forced to rotate by the torsion spring, the drive nut is also rotated, whereby the plunger rod is moved proximally for expelling a dose of medicament.

2. The medicament delivery device of claim 1, wherein the turnable dose setting member comprises a circumferentially extending ratchet configured to co-act with a corresponding circumferentially extending ratchet on the distal housing part, and the ratchets are shaped such that the dose setting member is rotated in only one direction.

3. The medicament delivery device of claim 2, wherein the dose setting member is resiliently movable in a longitudinal direction of the hub by a first resilient member arranged between a circumferential ledge of the distal housing part and a circumferential ledge of the dose setting member for forcing the ratchets in connection with each other, such that when the dose setting member is pulled against a force of the first resilient member, the ratchets move out of contact with each other and enable the dose setting member to be turned back to reset a dose.

4. The medicament delivery device of claim 1, wherein an outer circumferential surface of the drive member includes indicia visible through a window on a circumferential surface of the dose setting member.

5. The medicament delivery device of claim 1, wherein the second end of the torsion spring is connected to the central hub of the drive member through a lock sleeve.

6. The medicament delivery device of claim 1, wherein the torsion spring is a clock spring.

7. The medicament delivery device of claim 1, further comprising an activation mechanism having an actuatable member with a lock member interactively connected to the second interacting devices of the drive' nut for locking the drive nut from rotation until activation of the actuatable member.

8. The medicament delivery device of claim 7, wherein the turnable dose setting member comprises a circumferentially extending ratchet configured to co-act with a corresponding circumferentially extending ratchet on the distal housing part, and the ratchets are shaped such that the dose setting member is rotated in only one direction.

9. The medicament delivery device of claim 8, wherein the dose setting member is resiliently movable in a longitudinal direction of the hub by a first resilient member arranged between a circumferential ledge of the distal housing part and a circumferential ledge of the dose setting member for forcing the ratchets in connection with each other, such that when the dose setting member is pulled against a force of the first resilient member, the ratchets move out of contact with each other and enable the dose setting member to be turned back to reset a dose.

10. The medicament delivery device of claim 7, wherein an outer circumferential surface of the drive member includes indicia visible through a window on a circumferential surface of the dose setting member.

11. The medicament delivery device of claim 7, wherein the second end of the torsion spring is connected to the central hub of the drive member through a lock sleeve.

12. The medicament delivery device of claim 7, wherein the torsion spring is a clock spring.

* * * * *